(12) United States Patent
Regnier et al.

(10) Patent No.: US 6,596,144 B1
(45) Date of Patent: *Jul. 22, 2003

(54) SEPARATION COLUMNS AND METHODS FOR MANUFACTURING THE IMPROVED SEPARATION COLUMNS

(75) Inventors: Fred E. Regnier, West Lafayette, IN (US); Bing He, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 259 days.

This patent is subject to a terminal disclaimer.

(21) Appl. No.: 09/699,674

(22) Filed: Oct. 30, 2000

Related U.S. Application Data

(63) Continuation of application No. 08/863,543, filed on May 27, 1997, now Pat. No. 6,156,273.

(51) Int. Cl.[7] .................... G01N 27/447; G01N 30/02; B03C 7/00
(52) U.S. Cl. .................. 204/601; 204/600; 422/70; 209/128
(58) Field of Search .............. 422/70, 99; 204/600, 204/601; 209/128, 158

(56) References Cited

U.S. PATENT DOCUMENTS

| | | | |
|---|---|---|---|
| 3,640,813 A | 2/1972 | Nerenberg | 204/615 |
| 4,587,020 A | 5/1986 | Nakagawa et al. | 210/658 |
| 4,980,057 A | 12/1990 | Dorn et al. | 210/198.2 |
| 5,116,495 A | 5/1992 | Prohaska | 210/198.2 |
| 5,194,133 A | 3/1993 | Clark et al. | 204/608 |
| 5,296,375 A | 3/1994 | Kricka et al. | 435/291 |
| 5,304,487 A | 4/1994 | Wilding et al. | 435/291 |
| 5,427,663 A | 6/1995 | Austin et al. | 204/180.1 |
| 5,486,335 A * | 1/1996 | Wilding et al. | 422/55 |
| 5,500,071 A | 3/1996 | Kaltenbach et al. | 156/272.8 |
| 5,632,957 A | 5/1997 | Heller et al. | 422/68.1 |
| 5,637,458 A | 6/1997 | Frankel et al. | 435/6 |
| 5,645,702 A | 7/1997 | Witt et al. | 204/501 |
| 5,646,048 A | 7/1997 | Templin et al. | 436/180 |
| 5,650,846 A | 7/1997 | Yin et al. | 356/318 |
| 6,156,273 A * | 12/2000 | Regnier et al. | 422/70 |
| 6,221,654 B1 * | 4/2001 | Quake et al. | 435/287.3 |

FOREIGN PATENT DOCUMENTS

| | | |
|---|---|---|
| WO | WO 93/22053 | 11/1993 |
| WO | WO 93/22054 | 11/1993 |
| WO | WO 96/07954 | 3/1996 |
| WO | WO 96/42012 | 12/1996 |
| WO | WO 97/22825 | 6/1997 |

OTHER PUBLICATIONS

Sobek et al., "A MicroFabricated Flow Chamber for Optical Measurements in Fluids", *An Investigation of Micro Structures, Sensors, Actuators Machines and Systems*, IEEE (1993), pp. 219–224. Feb.

* cited by examiner

Primary Examiner—Nam Nguyen
Assistant Examiner—Alex Noguerola
(74) Attorney, Agent, or Firm—Testa, Hurwitz & Thibeault, LLP

(57) ABSTRACT

A separation column for use in a separation process such as chromatography, electrochromatography and electrophoresis is described. The separation column includes multiple collocated monolith support structures and interconnected channels defined by the support structures. The monolith support structures and interconnected channels are created on a substrate using an isotropic etching. The separation column also includes a cover plate disposed on the etched surface of the substrate, creating an enclosed separation column.

36 Claims, 10 Drawing Sheets

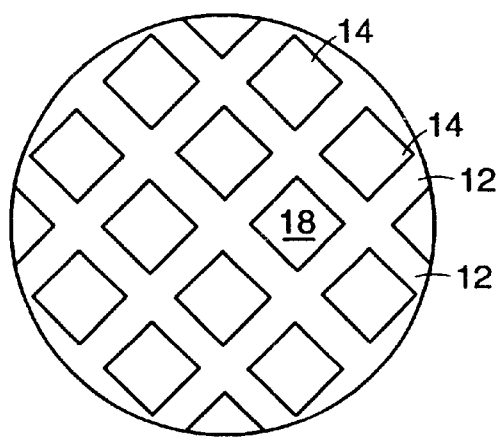
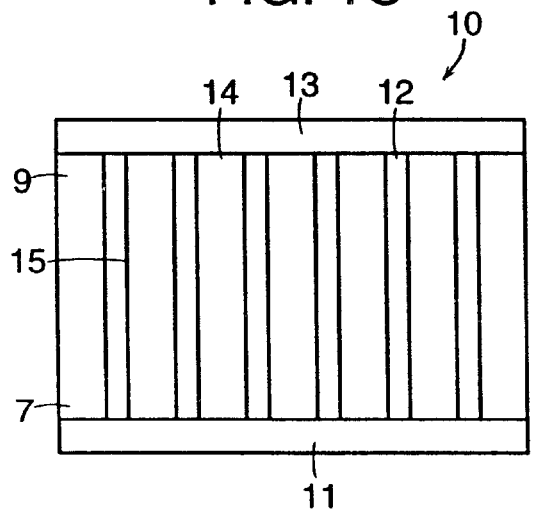
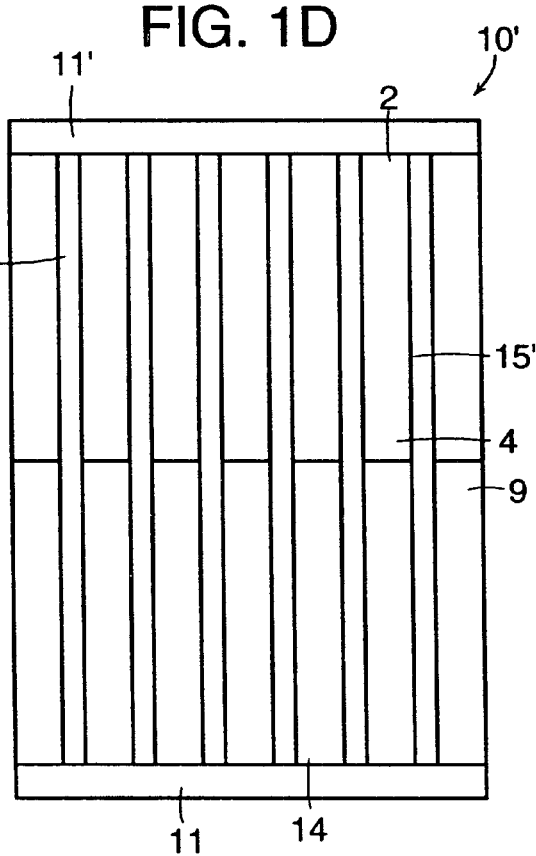

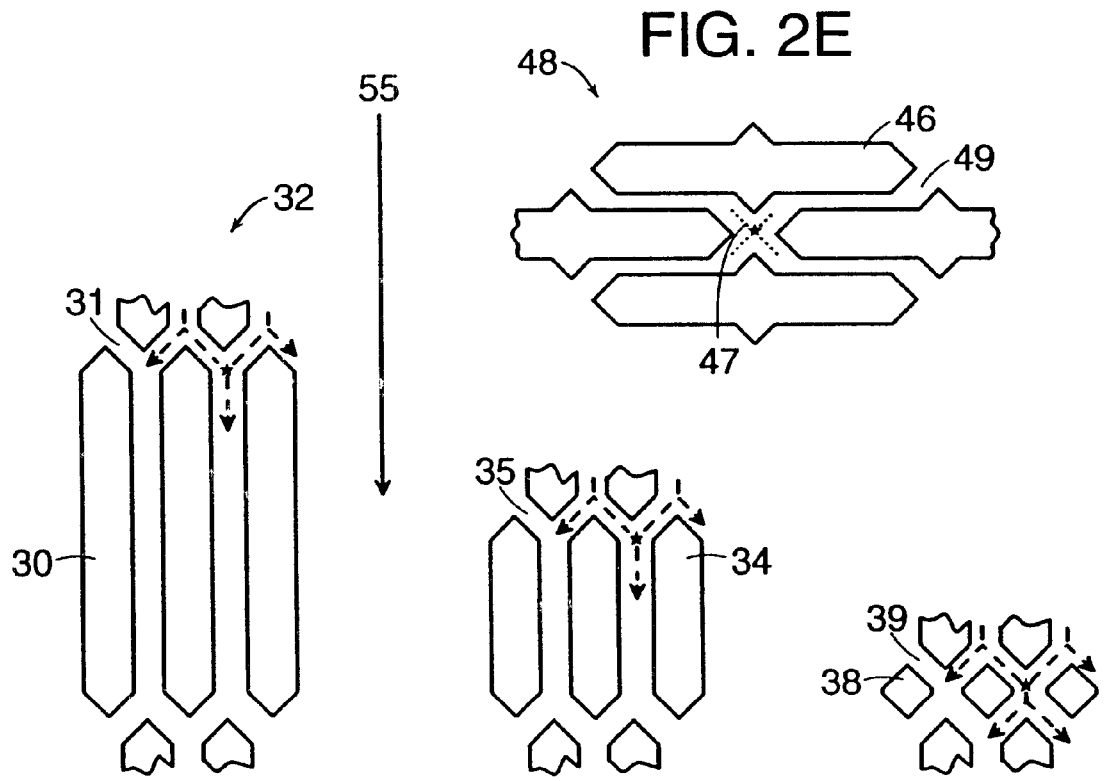
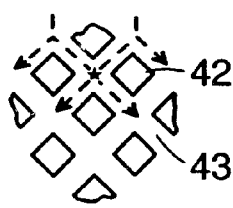
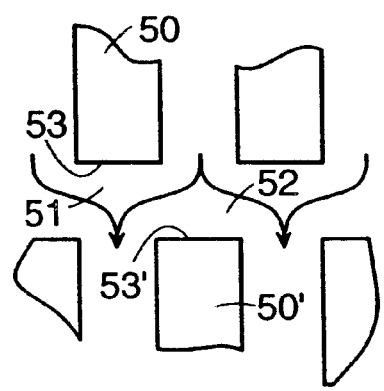
FIG. 2A  FIG. 2B  FIG. 2C
FIG. 2D
FIG. 2E
FIG. 2F

SEPARATION COLUMNS AND METHODS FOR MANUFACTURING THE IMPROVED SEPARATION COLUMNS

RELATED APPLICATIONS

This is a continuation of U.S. Ser. No. 08/863,543, filed May 27, 1997, now U.S. Pat. No. 6,156,273, the entire disclosure of which is incorporated by reference herein.

STATEMENT REGARDING FEDERALLY SPONSORED RESEARCH

The United States government may have certain rights in this invention as the invention was developed in part with the United States government support under grant number 5RO1GH515 74-03.

THE FIELD OF THE INVENTION

The invention relates to separation apparatus and more specifically to separation columns and methods for manufacturing separation columns for use in separation processes.

BACKGROUND

Separation-based analytical methods, including chromatography, electrophoresis and electrochromatography are useful in determining individual samples in complex mixtures. In chromatography, a sample to be analyzed is introduced into a separation column, which contains a mobile phase and a stationary phase. Components of the sample separate as the sample passes through the column due to differences in interaction of the different components with the stationary phase.

Electrophoresis is a separation technique that is based on the mobility of ions in an electric field. In capillary electrophoresis, a sample is placed in a capillary tube, which contains an electrophoretic medium. Upon application of an electric field across the capillary, components of the sample migrate at different rates towards the oppositely charged ends of the capillary based on their relative electrophoretic mobilities in the medium. Electrochromatography is a combination of chromatography and electrophoresis, in which the mobile phase is transported through the separation system by electroosmotic flow (EOF).

Separation of samples in complex mixtures based on analytical systems that are capable of executing large numbers of separations would be useful. In particular, separation technologies that process multiple samples quickly and multi-dimensional separations for each sample are desired. However, existing separation technologies do not generally have these features. Liquid chromatography systems do not readily adapt to parallel processing because adding multiple precision pumps and valves, necessary to deliver multiple samples, is both impractical and expensive. Multi-dimensional chromatography separations are feasible by transferring components from a first separation column to a second separation column with rotary valves. However, such processes can be very slow. Parallel processing for capillary electrophoresis has been achieved using microfabrication, which allows multiple channels to be placed on a single chip. However, a limitation is that no methods are available to introduce a large number of samples into the channels and to rapidly clean the sample metering channels between separations.

The present invention relates to separation columns for use in chromatography, electrochromatography and electrophoresis, which overcome the sample limitations of the existing separation systems. The separation columns of the present invention also require orders of magnitude less solvent and analyte, thereby diminishing the sample disposal problem.

SUMMARY OF THE INVENTION

In one aspect, the invention relates to a separation column, which is used in a separation process. The separation column includes multiple collocated monolith support structures and interconnected channels defined by the support structures. The collocated monolith support structures are arrayed in two dimensions to define channels that periodically split and merge. In one embodiment, the support structures are in communication with each other at the first end of each support structure and a cover plate is in communication with the support structures at the second end of each structure.

In another aspect, the invention relates to a method for manufacturing a separation column, which is used in a separation process. According to the method, a substrate is patterned to designate the areas of the substrate to be etched. The patterned substrate is etched to create multiple collocated monolith support structures arrayed in two dimensions and interconnected channels defined by the support structures. In one embodiment, a cover plate is attached on a surface of the created support structures to enclose the separation column. In another embodiment, the substrate is etched to create the support structures and the channels that are substantially uniform in shape and size. In yet another embodiment, the substrate is etched to create interconnected channels, in which each channel has an aspect ratio of from about 5 to about 100. The aspect ratio as used herein is the ratio of the depth to the width of a channel between adjacent monolith structures, where the depth is a dimension perpendicular to the surface of the substrate and the width is a dimension parallel to the surface of the substrate and perpendicular to the flow direction in the channel.

In another aspect, the invention relates to a separation column. The separation column includes an inlet, a separation region and an outlet. The separation region is in communication with the inlet and comprises a plurality of collocated monolith support structures that are arranged in two dimensions. The support structures define a plurality of interconnected channels that sequentially split and merge. The outlet is in communication with the separation region.

In yet another aspect, the invention relates to a separation apparatus. The separation apparatus includes a separation column, a plurality of reservoirs for mobile phases or buffers and a sample reservoir. The separation column has multiple collocated support structures arrayed in two dimensions and interconnected channels defined by the support structures. The reservoirs are in communication with the separation column. The sample reservoir is in communication with the separation column. In one embodiment, the separation apparatus also includes a pump for pumping a mobile phase from a reservoir through the separation column. In another embodiment, the separation apparatus also includes an electrophoresis apparatus.

In still another aspect, the invention relates to a method for separating components of a sample. According to the method, a medium solution is introduced into a separation column, which includes multiple collocated monolith support structures and interconnected channels defined by the support structures. A sample to be analyzed is also introduced into the separation column. The solution and the sample pass through the separation column in multiple streams and the multiple streams periodically intercouple. Components of the sample are separated as the sample passes through the column. The components may be separated by electrophoretic mobility, electroosmotic flow (EOF), EOF and partitioning with a stationary phase, micellar electrokinetic chromatography, or a combination of these.

BRIEF DESCRIPTION OF THE DRAWINGS

These and other advantages of the invention may be more clearly understood with reference to the specification and the drawings, in which:

FIG. 1B shows a detailed planar view of a portion of the embodiment of the separation column of FIG. 1A.

FIG. 1C shows a cross-sectional view of the section of the embodiment of the separation column of FIG. 1A cut through the line 1C'–1C".

FIG. 1D shows a cross-sectional view of a section of an embodiment of the separation column of FIG. 1A.

FIGS. 2A, 2B, 2C, 2D, 2E and 2F depict a plan view of several embodiments of the monolith support structures useful in the embodiment of the invention shown in FIG. 1A.

DESCRIPTION OF THE PREFERRED EMBODIMENT

Figure 1A:
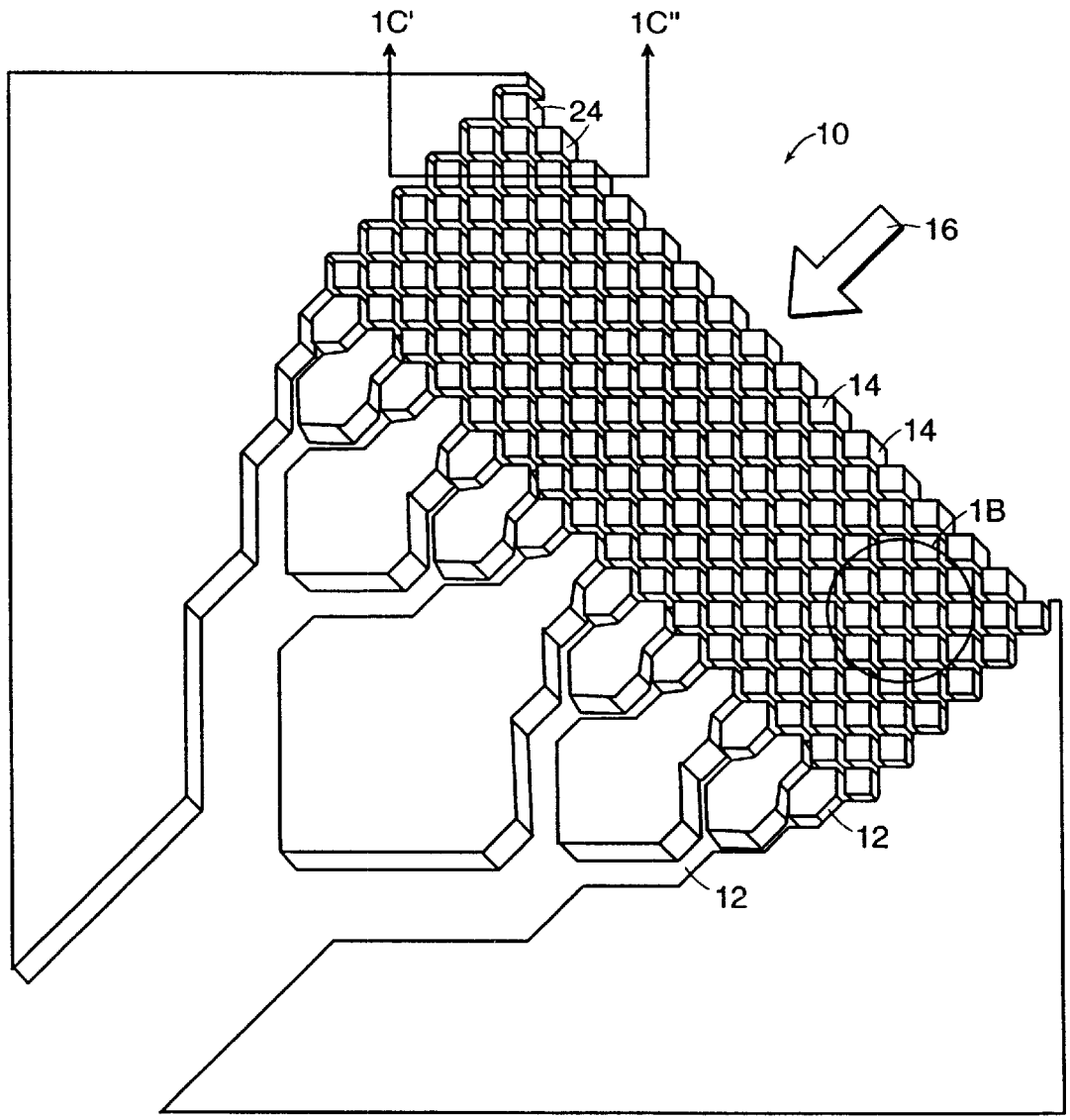
FIG. 1A shows a perspective view of an embodiment of a separation column with collocated monolith support structures constructed in accordance with the invention.

Referring to FIGS. 1A, 1B, 1C, and 1D, a separation column 10, constructed in accordance with the invention, includes a number of collocated monolith support structures 14 defining a series of interconnected microchannels 12. The term "collocated" refers to a side by side placement. The term "monolith" refers to a single structure, including a structure that forms a single piece by attachment. The collocated monolith support structures 14 are arrayed in two dimensions and define channels 12 that periodically merge and split. The collocated monolith support structures 14 are fabricated on a substrate 11, and hence are attached to one another at a first end 7 by the substrate 11. However, the remainder of each monolith structure 14 is physically separated from each other forming interconnected channels 12. In the embodiment of FIG. 1C, a cover plate 13 is disposed over and bonded to the second end 9 of the collocated monolith support structures 14 enclosing the separation column 10. In the embodiment of FIG. 1D, a second group of monolith structures 2 being a mirror image of a first group of monolith support structures 14 is disposed over the first group of monolith support structures 14 such that the second end 9 of a monolith structure 14 of the first group joins the second end 4 of a monolith structure 2 of the second group, thereby forming channels 6 that are twice as deep. The dimensions of the collocated monolith structures 14 are typically about less than 100 µm in height and 1000 µm$^2$ in cross-sectional area 18 for chromatography applications. The height of the monolith structures 14, however, may be much longer, for example 500 µm, in electrophoresis applications. In this context, height refers to the distance from a first end 7 to a second end 9 of a monolith structure 14, perpendicular to the surface of the substrate 11. Since the present height of a monolith structure 14 is limited by existing etching technologies, the height is expected to increase with advances in such technologies. Cross-sectional area 18 refers to the area of a monolith structure 14 measured parallel to the plane of the substrate 11. The distance between any two adjacent monolith structures 22 is approximately equal and typically does not exceed about 10 µm at any point in chromatography applications. In electrophoresis applications, the distance may be much wider, for example 100 µm.

In the embodiments of FIGS. 1A, 1B, 1C and 1D, the monolith structures 14 are substantially identical in size and shape in the separation column 10 and the channel walls 24 are as nearly vertical as possible, such that width of the channel 12 along an entire channel is approximately constant. With capillary electrophoresis, channels 12 do not necessarily have to be vertical. However, with pressure driven, open channel liquid chromatography, widths 22 along an entire channel should be constant, because a flow rate in parallel channels (i.e., at the same position along the column length) in a pressure driven system is proportional to channel width 22. Therefore, flow rates that are not constant because of the variations in channel width 12, contribute to band spreading beyond that of a normal parabolic flow profile of a liquid passing over a surface.

Collocated monolith structures 14 defining nearly vertical interconnected channels 12 are created by a variety of techniques. Suitable etching techniques, for example, include anisotropic etching techniques such as reactive ion etching, electron beam etching and LIGA (Lithographie Galvanoformung Abformung). These etching techniques are well known in the art. LIGA is a process that allows fabrication of three dimensional structures having high aspect ratios. The process involves four steps: irradiation, development, electroforming and resist stripping. The irradiation step involves irradiating a resist using laser, electron-beam or X-ray from a synchrotron radiation source. In the development step, a pattern is transferred into the resist and the resist is etched to reveal three dimensional structures comprising the resist material. In the electroforming step, a metallic mold is produced around the resist structures by electroplating. In the final step, the resist is stripped to reveal channels. Anisotropic wet etching may also be used to create the channels 12. Anisotropic wet etching, however, requires specific types of substrates. For example, the substrate must be crystalline and etching occurs along a specific axis.

In fabricating the separation column 10, first, a substrate 11 is provided to create microfabricated collocated monolith structures 14. Examples of materials suitable for substrates 11 include, but are not limited to, silicon, quartz, glass, and plastic. The substrate 11 is patterned to designate areas to be etched. The patterned substrate is etched to create collocated monolith support structures 14 and interconnected channels 12 defined by the support structures 14. In a preferred embodiment, the substrate 11 is etched by a process that provides channels 12 with uniform width.

Subsequent to etching the substrate 11, surfaces of the monolith structures 15 may be treated to provide interactions between the surfaces 15 and a sample passing through the separation column 10, thereby inducing separation of components of the sample. For example, surfaces of the monolith structures 15 may be coated with specific binding analytes by coating technologies known to or to be discovered by those skilled in the art. U.S. Pat. No. 5,030,352, which describes a method of coating a surface of a separation column, is incorporated herein by reference. A coating technology for coating surfaces of the monolith structures 15 is not an aspect of the present invention. The coating may be thin or thick. Materials placed on the surfaces of the monolith structures 15 include, for example antibodies, cationic or anionic coatings, chelators, organic coatings including complex sugars and heparin, gels, fimbriae, and reverse phase coating such as C18. The specific binding analyte may be immobilized or entrapped in the channels 12.

In one embodiment shown in FIG. 1C, a cover plate 13 is added to create an enclosed separation column 10. The cover plate 13 may be attached by placing the cover plate 13 in contact with the etched surface of the substrate 11 and causing the cover plate 13 to bond to the etched substrate 11. In the cases of a silica, glass or quartz cover plate 13, fusing creates cohesive bonding of very smooth surfaces. A cover plate 13 can be fused to the etched substrate 11 by allowing the two pieces to come in contact, placing them in an oven, and gradually raising the oven temperature. In some cases, bonding may take place at around 90° C. In other cases, the oven temperature may have to be raised up to 1000° C. Alternatively, for a silica or glass substrate, bonding may take place at room temperature by spinning on a layer of sodium silicate solution containing 5–7% solids and placing the substrate 11 and the cover plate 13 in contact.

In another embodiment shown in FIG. 1D, a second etched substrate 11' having a mirror image of the first etched substrate 11 is disposed over and bonded to the first etched substrate 11 forming a separation column 10' with channel depth that is twice as long. In either case, a bonding process need not produce a continuous bond between the support structures 14, 2 or the support structures 14 and the cover plate 13. However, the resulting bond must seal the channels 12 such that a solution inside the channels cannot communicate with the outside world along the interface of the two substrates. Any other suitable bonding technique may be used without departing from the spirit of the present invention.

In application, a separation apparatus includes a plurality of reservoirs and at least one sample reservoir in communication with the separation column 10. In one embodiment, the separation apparatus includes a pump for pumping a mobile phase from a reservoir through the separation column 10. In another embodiment, the separation apparatus includes an electrophoresis apparatus in electrical communication with the separation column 10. The electrophoresis apparatus applies a potential across the separation column 10 for separating components of a sample passing through the separation column 10. In still another embodiment, the separation apparatus includes a detector in communication with the separation column 10 for detecting components separated by the separation column 10. The detector, for example, may be a mass spectrometer or an infrared detector. The operations of a mass spectrometer and an infrared detector are well known in the art. U.S. Pat. Nos. 5,498,545 and 5,045,694, which describe mass spectrometers are incorporated herein by reference.

In the embodiments 1A and 1B, the collocated monolith support structures 14 have tetragonal cross-sectional areas 18. Tetragonal or hexagonal cross-sectional geometries are preferred over other geometries (e.g., triangular), because tetragonal or hexagonal geometries can create substantially rectangular interconnected channels 12 having high aspect ratios, as well as providing channels that are substantially parallel to the longitudinal axis of the separation column 10 when properly oriented. An aspect ratio is the ratio of the lengths of the depth to the width of a channel 12 between adjacent support structures 14, where the depth is the dimension perpendicular to the surface of the substrate 11 and the width is the dimension perpendicular to the flow direction in the channel 12. Rectangular channels, as defined by a plane perpendicular to the substrate, having high aspect ratios, are preferred over traditional cylindrical channels for the following reasons. If a rectangular channel having a high aspect ratio (i.e., >, >5) and a traditional cylindrical channel with the same cross-sectional areas are used for liquid chromatography, the distance that a sample must travel to contact the maximum surface area of a stationary phase is shorter for the rectangular channel than it is for the traditional cylindrical channel. Likewise, if a rectangular channel and a cylindrical channel with same cross-sectional areas are used in electrokinetically driven separation systems, the distance that a heated solvent must travel to reach the maximum area of heat dispersing surface is shorter with a rectangular channel having a high aspect ratio than it is with a cylindrical channel. Channels that are substantially perpendicular to the longitudinal axis 16 of the separation column are not preferred, since they will be filled with stagnant pools of mobile phase and cause peak dispersion by the limitations of stagnant mobile phase mass transfer. This phenomenon is widely described in chromatographic systems packed with porous particles, which are filled with stagnant mobile phases. Tetragonal and hexagonal cross-sectional geometries are preferred, since they can provide channels that are substantially parallel, or at least not substantially perpendicular, to the longitudinal axis of the separation column 10, when properly oriented.

Other non-limiting, cross-sectional geometries for collocated monolith support structures 14 that create rectangular channels are shown in FIGS. 2A to 2F. Although columnar monolith structures having circular cross-sections may be created, they are less desirable than tetragonal or hexagonal geometries, because the intercolumnar channels created by the columnar structures will not be as uniform as those created by tetragonal or hexagonal geometries. The structures shown in the FIGS. 2A to 2F have the advantage in that they may be closely packed and still have uniform and controllable channel dimensions between monolith structures.

According to the invention, the interconnected channels 12 have an aspect ratio of greater than 5 and more preferably greater than 10. Greater aspect ratios are possible by etching the substrate 11 deeper. The channel width is generally in the range of 1–10 $\mu$m for chromatography applications. Although a separation column 10 having channel widths of less than 1 $\mu$m may be desirable to reduce band broadening in chromatography, other operational problems such as plugging and high pressure requirements exist with such narrow columns.

In a preferred embodiment, the separation column 10 has a first group and a second group of channels 12, where the channels in each group are parallel to each other and the channels in the first group intersect with the channels in the second group. Where the channels 12 intersect, the point of intersection preferably is deeper than it is wide.

Determination of the depth and the aspect ratio of a channel 12 involves a compromise. A longer channel depth is useful in pressure driven separation systems, because mobile phase volume is increased allowing more sample to be carried in a channel. However, in electrically driven separation systems, heat transfer becomes limited with a longer channel depth. When operating at high voltage, joule heating causes transaxial thermal gradients to develop along the depth of channels having high aspect ratios. In a dense channel system where the aspect ratio of each channel goes beyond 10–20 and the channel depth is greater than 20 $\mu$m, heat transfer to the surface of the chip can become limiting, unless channel density is decreased.

Determination of the channel width also involves a compromise. Channels 12 having widths smaller than 1–2 $\mu$m increase the transfer rate of sample components to the channel surfaces where the components can interact with the surface. However, in a pressure driven system, the operating pressure for a separation column 10 with such narrow channels 12 is large, making it difficult to get liquid into the channel network, and more susceptible to plugging.

In one embodiment, the substrate 11 is etched to create interconnected channels having an aspect ratio of from about 5 to about 100. Even higher aspect ratios may be desirable, but is beyond the limits of current microfabrication technology. In a preferred embodiment, the aspect ratio of a channel 12 in a voltage driven separation system is from about 10 to about 20, whereas the aspect ratio of a channel 12 in a pressure driven separation system is greater than 20. Current typical microfabrication technology allows resolution in the production of masks and etching to about 0.1 $\mu$m. Therefore, the lower limitation on a channel width is approximately 0.5±0.1 $\mu$m and the upper limitation on the depth of such channel is approximately 10 $\mu$m in chromatographic systems. Separation columns having channels of such dimensions, fabricated with existing technologies, however, can exhibit channel heterogeneity, which leads to peak dispersion. Channel heterogeneity, however, is caused by fabrication limitations and not design, and therefore is expected to improve as fabrication technologies advance.

According to the present invention, geometry and size of the collocated monolith structures 14 and the interconnected channels 12 may be selected to optimize specific functions. For example, in one embodiment, separation columns are designed to optimize interchannel coupling. Interchannel coupling refers to mixing of streams from multiple channels to average heterogeneity in flow and peak dispersion between individual channels across many channels. The dominant concern with multi-channel systems is that the channels may not be identical in terms of migration velocity and fluid dynamics. The separation columns of the present invention overcome this concern by mixing fluid from adjacent channels at periodic intervals along the length of the separation system.

FIGS. 2A to 2F show examples of collocated monolith support structures 30, 34, 3 8, 42, 46, 50 for achieving interchannel coupling. The illustrations in FIGS. 2A to 2F suggest that streams from adjacent channels will completely merge and mix, then spread laterally at the channel junctions 31, 35, 39, 43, 47, 51 into down-stream channels. However, in reality, incomplete mixing is likely at high mobile phase velocity. Three types of interchannel geometry to achieve intercoupling are revealed in FIGS. 2A to 2F. FIGS. 2A, 2B and 2C show a (Y) shape configuration for interchannel coupling, FIGS. 2D and 2E show an (X) shape configuration for interchannel coupling, and FIG. 2F shows a (T) shape configuration for interchannel coupling. The T shape configuration in FIG. 2F may be used to achieve interchannel coupling, but is nota preferred geometry. It has been observed that since adjacent channels in the T shape configuration intersection in a horizontal line and not a point, a nonstreamline flow results. Stagnant pools of liquid 51, 52 in the channel adjacent a bottom surface 53 of a monolith structure 50 and a top surface 53' of a monolith structure 50' accumulate. The bottom surface 53 is the surface of a monolith structure 50 perpendicular to the longitudinal axis 55 and the last surface of the monolith 50 to come in contact with a component passing through the column. The top surface 53' is the surface of a monolith structure 50' also perpendicular to the longitudinal axis 55 and the first surface of the monolith 50' to come in contact with the component passing through the column. Samples will diffuse into and out of these stagnant pools, and in the course of doing so, band spreading will result. In a preferred embodiment, monolith support structures 30, 34, 38, 42, 46 define channels 31, 35, 39, 43, 47 that intersect in X or Y shape configurations.

The geometry of monolith support structures affects interchannel coupling in another manner. Monolith support structures 30, 34 shown in FIGS. 2A and 2B result in less interchannel coupling than monolith support structures 38, 42 shown in FIGS. 2C and 2D. Assuming that two separation columns have equal length, with one column having support structures 30 shown in FIG. 2A and the other having support structures 38 shown in FIG. 2C, a sample in the first column 32 must travel further before interchannel coupling and encounters slightly fewer opportunities for interchannel coupling. This is because the support structures 30 in FIG. 2A are elongated as compared to the support structures 38 in FIG. 2C. The monolith geometries 30, 34 represented in FIGS. 2A and 2B are preferred when the degree of channel homogeneity is high, such that not much interchannel coupling is required. On the other hand, when there are interchannel differences in either the rate of flow or peak dispersion caused by faulty fabrication, fouling during operation, leaching of organic surface coatings, or some other type of aging, structures similar to the ones shown in FIGS. 2C and 2D are preferred because they provide more interchannel coupling. The monolith structures 30, 34 in FIGS. 2A and 2B have a length that is substantially longer than the width. The monolith structures 38, 42 in FIGS. 2C and 2D, have a length that is substantially equal to the width. The length is the dimension parallel to the longitudinal axis 55 of the separation column and the width is the dimension perpendicular to the longitudinal axis 55 of the separation column, where both dimensions are parallel to the surface of the substrate. The net effect of interchannel coupling is that heterogeneity between channels can be "averaged" or distributed across many channels as a sample migrates through the system.

In another embodiment, referring to FIG. 2E, a separation column 48 is designed to increase separation efficiency per unit length of the column 48. Separation efficiency is increased by creating monolith structures 46 and channels 49 that provide greater lateral migration relative to longitudinal migration between intercoupling. The monolith structures 46 have a length that is substantially shorter than the width. The net effect is that the migration distance of a sample through a longitudinal unit length of this column 48 is increased. This embodiment has properties similar to the serpentine channel columns existing in the prior art. Serpentine channel columns are used to increase the migration distance of a sample within the limited space available on a chip. The problem with the serpentine channel approach is the "race track" effect caused by the corners. The "race track" effect refers to the effect of components of a sample traveling near the inner surface of the corner covering a shorter distance than components traveling near the outer surface of the corner. The difference in distance covered can add to zone broadening. The great advantage of the embodiment shown in FIG. 2E is that it accomplishes efficiency per unit length but by using multiple channels and interchannel coupling, overcomes the "race track" effect. The embodiment of FIG. 2E also provides larger capacity with channels of the same width.

In yet another embodiment, the separation column of the invention is designed to maximize heat dissipation. An electrophoretic current applied to a separation column causes joule heating. Joule heating contributes to band spreading by creating thermal gradients, which produce transchannel convection. According to the present invention, heat is dissipated through the monolith support structures, which are in communication with a substrate or a cover at both ends. The separation columns of the present invention maximize heat dissipation in the following ways. First, heat dissipation is maximized by creating collocated monolith support structures and interchannels with high surface to volume ratio. Surface area refers to total wall space adjacent a single channel. Volume refers to volume of a single channel. Second, monolith structure mass to channel volume ratio is increased. Third, channel density in a separation column is minimized. Channel density can be minimized through monolith geometry. In a preferred embodiment, monolith structures with square cross-sectional areas are used to minimize channel density. Finally, channel height is minimized.

Figure 3A:
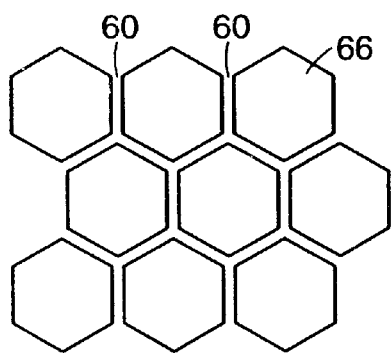
FIGS. 3A, 3B, 3C and 3D depict a plan view of several additional embodiments of the monolith support structures useful in the embodiment of the invention shown in FIG. 1A.
Figure 3B:
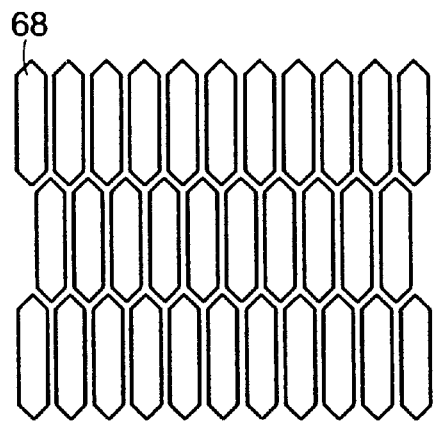
Figure 3C:
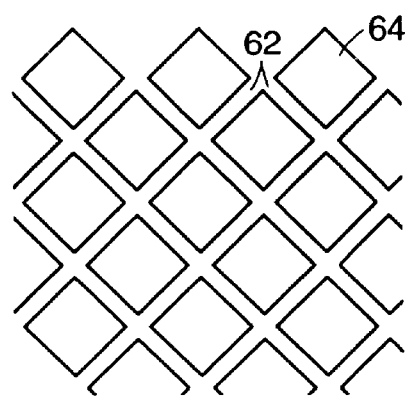
Figure 3D:
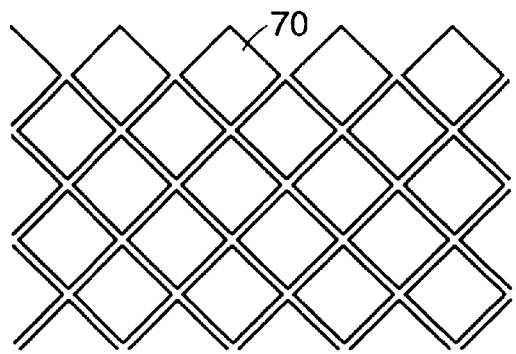

Narrow channels between monoliths having tetragonal and hexagonal cross-sections are generally suitable for heat dissipation, as they provide both a large surface area to liquid volume ratio per channel and a low density of channels distributed throughout a column. Referring to FIGS. 3A and 3C, narrow channels 60, 62 between tetragonal monoliths 64 and hexagonal monoliths 66 meet these criteria. However, the monolith geometry shown in FIG. 3A is preferred over the monolith geometry 66 shown in FIG. 3B, because the monolith geometry 66 in FIG. 3A provides lower channel density and higher monolith mass to channel surface area than the monolith geometry shown in FIG. 3B. The monolith 70 shown in FIG. 3D is preferred over the monolith 64 shown in FIG. 3C for the same reasons.

In yet another embodiment, separation columns are designed to minimize band spreading caused by a parabolic velocity distribution of a solution passing through the column. Parabolic velocity distribution in liquid chromatography becomes worse as the width of the separation column increases. The distance between adjacent support structures is minimized to reduce band spreading without encountering operational problems. In a preferred embodiment, the minimum channel width is about 1 $\mu$m.

Figure 4A:
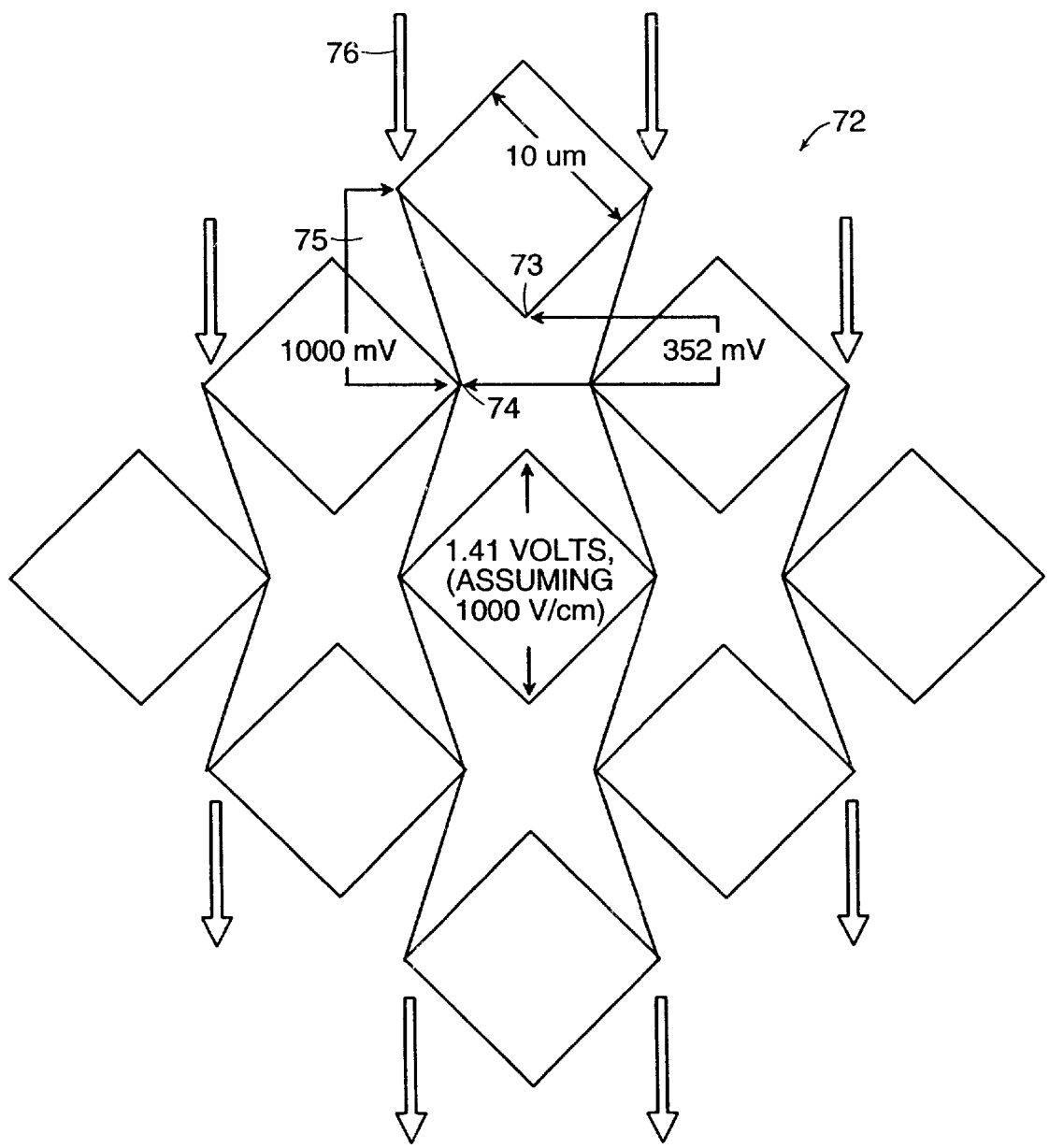
FIGS. 4A and 4B are highly schematic diagrams of the diagonal field line effect in various embodiments of the present invention.
Figure 4B:
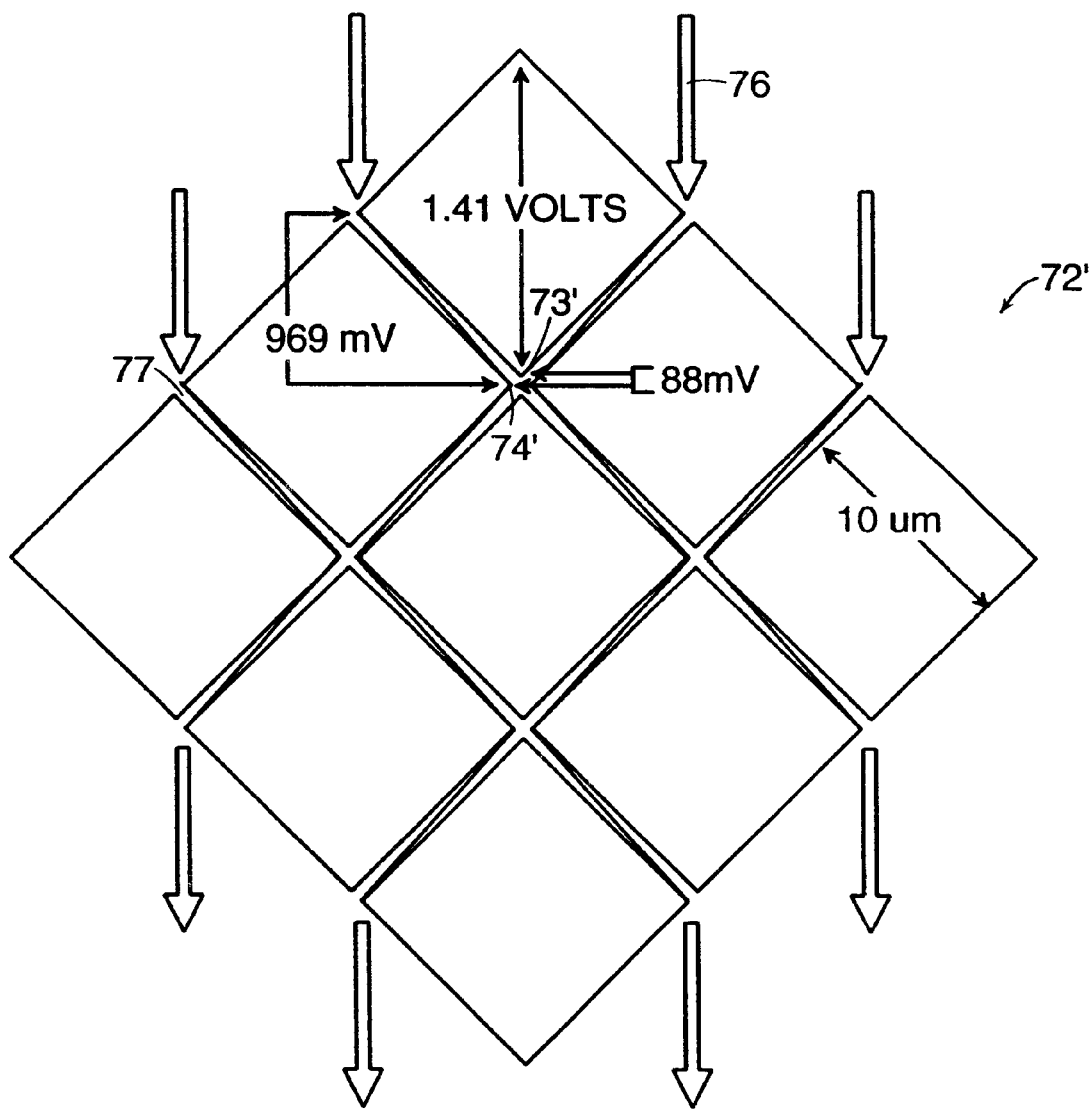

In yet another embodiment, separation columns in which the flow is electroosmotically driven are designed to minimize flow heterogeneity. Electroosmotic flow (EOF) refers to movement of liquid inside a separation column due to application of an electric field. The velocity of electroosmotic flow is related to a zeta potential generated at the surface of the column, the dielectric constant of the solution and the viscosity of the double layer formed at the surface of the column. Although there are localized regions of inhomogeneity in a zeta potential, EOF in a 10–100 cm open tubular capillary is relatively uniform. Referring to FIGS. 4A and 4B, EOF in a collocated monolith support structure system 72 differs from that in a single open tubular capillary. For example, there is the difference in lateral (or radial) electrical potential. Maximum electrical potential will be found where the field lines take the shortest route between the system electrodes. The electric potential is thought to be uniform across the separation channel in a single, long, open tubular capillary for this reason. In contrast, the shortest route between the electrodes in the collocated monolith support structure systems 72, shown in FIGS. 4A and 4B is to cut diagonally across channels 75, 77 that are not parallel with the electric field 76 in the system. Because there is a slightly higher potential on one side of the channel, it is expected that EOF on that face of the channel will be higher. In a system operating at 1000 V/cm (0.1 V/$\mu$m), there is a potential drop of approximately one volt along the length of a channel that is 10 $\mu$m long. A channel length is a dimension parallel to the surface of the substrate and parallel to the direction of flow,inside the channel. It is seen in FIGS. 4A and 4B that the diagonal nature of the channels 75, 77 can cause a vertical voltage differential of 88–352 mV at the positions 73, 73' and 74, 74' of individual channels 75, 77. It is probable that this diagonal field effect will induce flow heterogeneity within channels 75, 77 which could impact interchannel coupling at the channel junctions. The diagonal field line effect is greater in the separation column having wider channels 75 shown in FIG. 4A and less in the separation column having narrower channels 77 shown in FIG. 4B. In a preferred embodiment, the separation column driven by electroosmotic flow has collocated monolith support structures defining long, narrow channels 77 as shown in FIG. 4B to minimize the diagonal field line effect.

In still another embodiment, separation columns are designed to maximize the ratio of the overall surface areas of the support structures to the overall volume of the channels, defined as the A/V ratio. In chromatography, increasing the A/V ratio is advantageous as it increases the phase ratio and loading capacity. Phase ratio is the ratio of the area of the surface on which the stationary phase is supported to the volume of the mobile phase. When the phase ratio is very small, components of a sample are not adequately retained to achieve separation and resolution. In electrophoresis, separation columns with a high A/V ratio dissipates heat caused by joule heating with greater efficiency.

According to the invention, the A/V ratio is maximized by making the channels as long as possible and the channel width as narrow as possible, and by minimizing the number of channel junctions. A single, long capillary would be ideal to maximize the A/V ratio, but there are other overriding advantages to multi-channel systems. Acceptable limits on the A/V ratio should not compromise other variables in the system. According to the invention, the channel length (l) to width (w) ratio exceeds 3 and preferably exceeds 5.

Figure 5A:
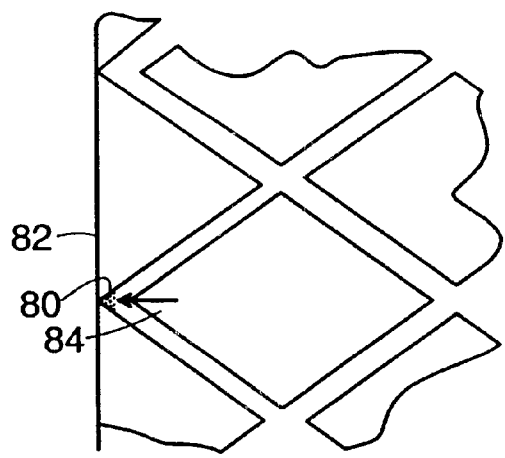
FIGS. 5A, 5B and 5C show a plan view of embodiments of the support structures for eliminating wall effects near the walls of a separation column.
Figure 5B:
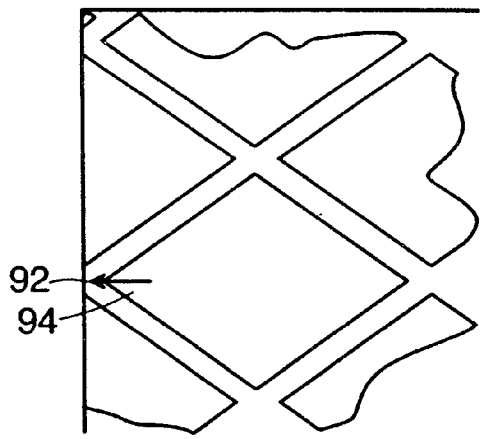
Figure 5C:
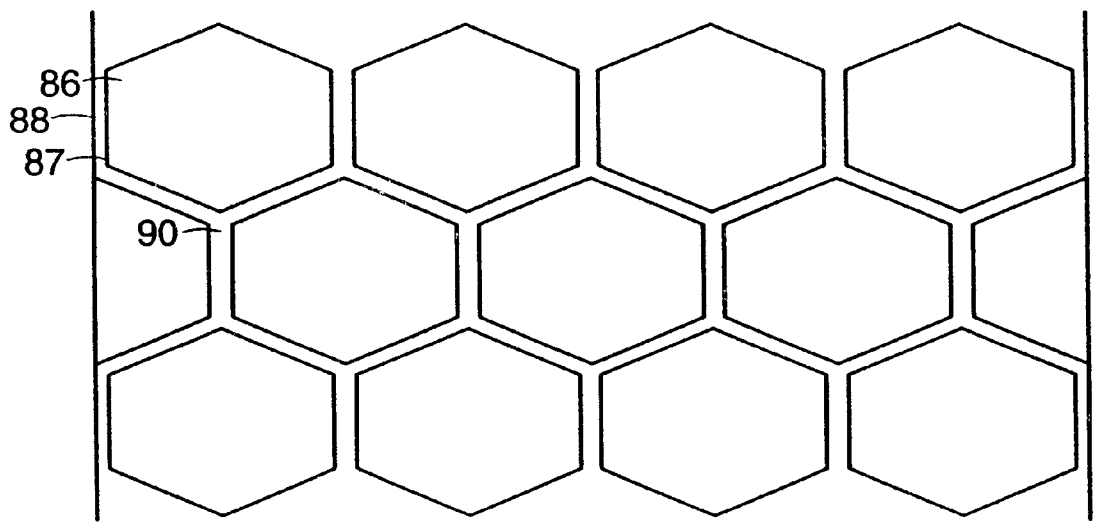

In still another embodiment, separation columns are designed to eliminate "wall effects." "Wall effects" refer to the potential for stagnant pools of liquid to form at the walls of separation columns comprising collocated monolith support structures. Referring to FIG. 5A, stagnant pools 80 of liquid can form between a wall 82 and a corner of a tetragonal monolith 84. In some respect, this is similar to the "race track" effect noted above and may contribute to peak dispersion. In the embodiment of FIG. 5C, the monolith 86 eliminates the potential for any dead spaces at the wall 88 such that the wall 88 is swept by the liquid flow. A hexagonal monolith geometry allows a flat side of a monolith 87 to be parallel to the wall 88 such that there is no dead space between the monolith 86 and the wall 88. At the same time, the hexagonal monolith 86 provides interchannel coupling by having a Y-shaped channel me, configuration 90. In the embodiment of FIG. 5B, rounding the corners during the etching process eliminates dead spaces 80 (shown in FIG. 5A) between the walls 92 and the corners of the tetragonal monoliths 94 and thereby also eliminating the "wall effects."

In prior art chromatography columns, the diameter of a column is many times larger (frequently >10X) than the diameter of the inlet or the outlet channel of the column. This presents several challenges. One challenge is to homogeneously distribute mobile phase and analyte laterally across the head of the column at the inlet without creating band spreading. Another challenge is to homogeneously collect the mobile phase and the analyte after they have traversed the length of the column without causing zonal dispersion. In packed microcolumns, this is frequently achieved by fusing microparticle silica particles at the column outlet. This process is very similar to the fusion process used to produce the "frit" in a flitted glass filter funnel. The problem with this approach is that it is very difficult to pack these particles uniformly and then fuse them inside the capillary. The "fused frit" approach has been reported to cause serious zonal dispersion because they are not uniform causing flow inhomogeneity.

Figure 6:
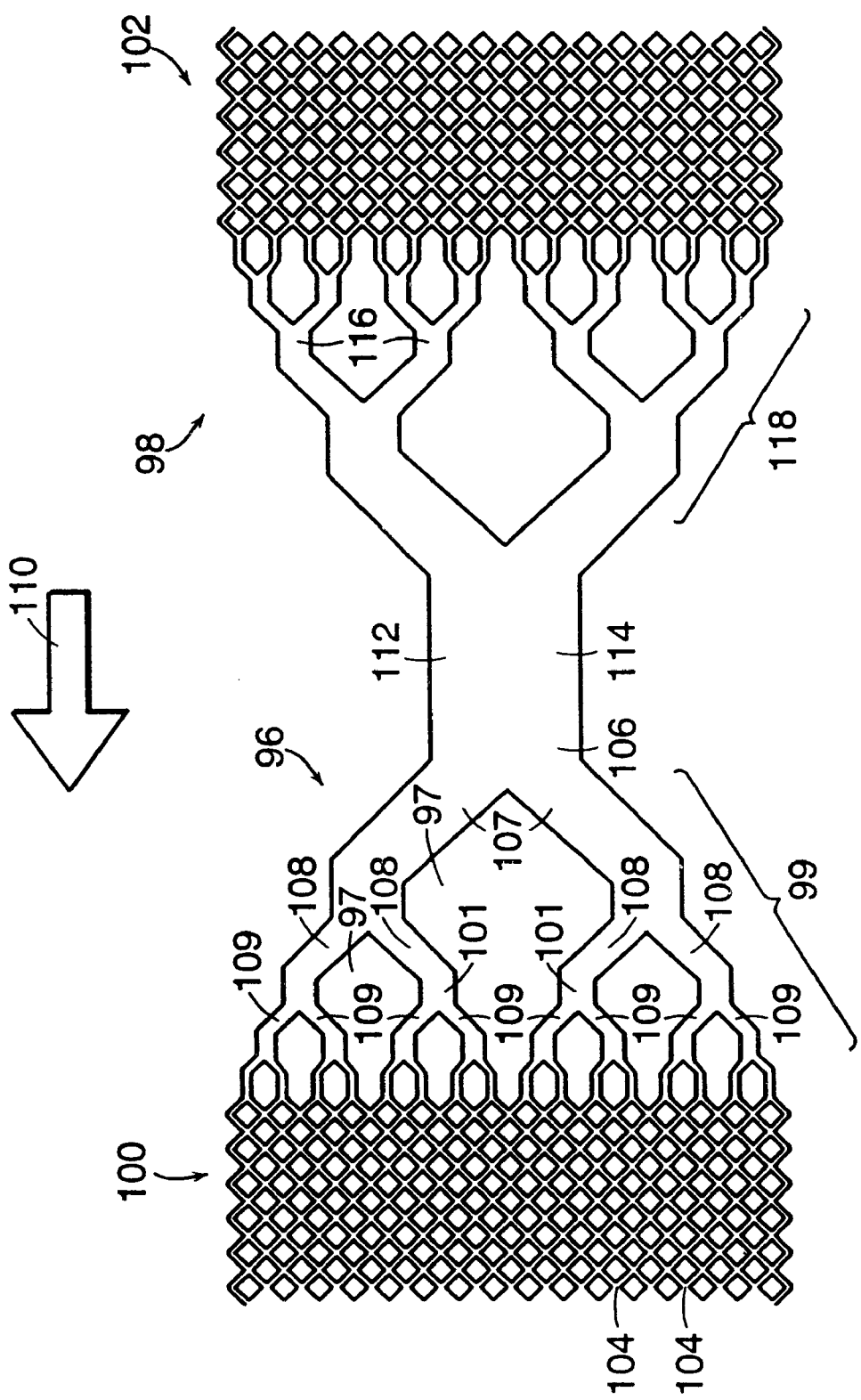
FIG. 6 shows a rendition of a plan view of an embodiment of a collocated monolith distributor of a second separation column interfaced with a collocated monolith collector of a first separation column.

Referring to FIG. 6, the present invention eliminates the need for column terminating frits because the monolith supports, which take the place of particles, are all fabricated on a single wafer and therefore are immobilized. However, there is the issue of distributing and collecting the mobile phase at the column ends 114. The invention addresses the fluid mechanics of homogeneously splitting and combining streams at the ends of separation columns 100, 102 by creating a collocated monolith distributor at an entry end of a separation column and a collocated monolith collector at an exit end of the separation column. In a multi-dimensional system, each separation column may comprise a collocated monolith distributor and a collocated monolith collector.

The concept behind the collocated monolith distributor 96 is to use monolith structures 97 to create a channel network 99, which sequentially splits a single channel into multiple channels by $X^n$ factor, where X is the number of channels that a single channel splits into and n is the number of times splitting takes place to provide communication between the channels 101 in the channel network 99 and the channels 104 in the separation column 100. In the inlet 96 disclosed in FIG. 6, a single stream 106 is first homogeneously split into two streams 107, the two streams 107 are split into four streams 108, the four streams 108 are split into eight streams 109, etc. The total number of channels (C) laterally across the inlet channel network 99 of the distributor 96 shown in the figure can be expressed by the equation $$C = 2^n$$

where n is the number of times the liquid stream splits. In a preferred embodiment, the channels 101 in the inlet channel network 99 splits by $2^n$ factor. Although it is possible to use splitting systems that follow $3^n$, $4^n$, or $X^n$ rule, it is more difficult to keep the path length of all channels equal without increasing tortuosity in some channels. However, these structures may be preferred in cases where a wider column layout is needed for higher sample capacity. With these embodiments, constant cross-sectional areas of channels are maintained by the addition of two monolith structures in between the channels.

Interchannel splitting provided by the inlet channel network 99 causes the same volume of liquid to reach all points in a lateral cross-section of the separation column 100 at the same time. Any system which causes this to happen will give homogeneous interchannel splitting in the delivery of the mobile phase and sample separation column. In a preferred embodiment, the inlet channel network 99 has channels of equal width, height, and length to achieve homogeneous interchannel splitting. In another embodiment, where the inlet channel network 99 has channels 101 with differing length and width, the length and width of each channel is adjusted such that equal volumes of liquid reach all points at the column inlet to maintain homogeneous interchannel splitting.

In one embodiment, cross-sectional areas of all channels 101 in the inlet channel network 99 are substantially equal. The cross-section area of a channel is perpendicular to the longitudinal axis 110 of the separation column. An advantage of this embodiment is that narrow channels 101 used throughout the network 99 minimizes "race-track" effects in channels that provide corners. Disadvantages of this embodiment are that liquid flowing into the separation column 100 have non-uniform velocities, which can cause zone broadening and increase degassing (bubble formation) from mobile phases in EOF pumped columns. Since all channels 101 are the same width, the total cross-sectional area of the channels double at each level of splitting in the $2^n$ system. The linear velocity of the mobile phase slows down as the mobile phase passes through subsequently split channels, since velocity is inversely proportion to cross-sectional area. Furthermore, the pressure will vary inversely with cross-sectional area.

In the embodiment shown in FIG. 6, the cross-sectional areas of the channels 101 in the inlet channel network 99 are sequentially halved as the number of channels 101 in the network 99 double at each level of splitting. This embodiment maintains the total cross-sectional area of the network across all planes, measured orthogonal to the longitudinal axis 110 of the separation column 100 to be substantially constant. Furthermore, channels at each split level have the same cross-sectional area. Advantages of this embodiment are that linear velocity of mobile phase and pressure drop are constant at all points in the system.

The monolith collector 98 is created in a manner similar to the monolith distributor 96. Adjacent channels 116 in the network 118 are sequentially combined by $X^n$ factor, where X is the number of adjacent channels 116 that combine into a single channel and n is the number of times combinations take place. Combinations take place until all channels are combined into a single column 112.

Therefore, a monolith distributor 96 or a monolith collector 98 having all channels with equal cross-sectional areas is preferred when the objective is to minimize intra-column zonal dispersion, i.e., no "race-track" effect, whereas a monolith distributor 96 or a monolith collector 98 with constant total cross-sectional area for channels in the same split level is preferred when the objective is to minimize extra column zonal dispersion, i.e., constant velocity and pressure.

Figure 7:
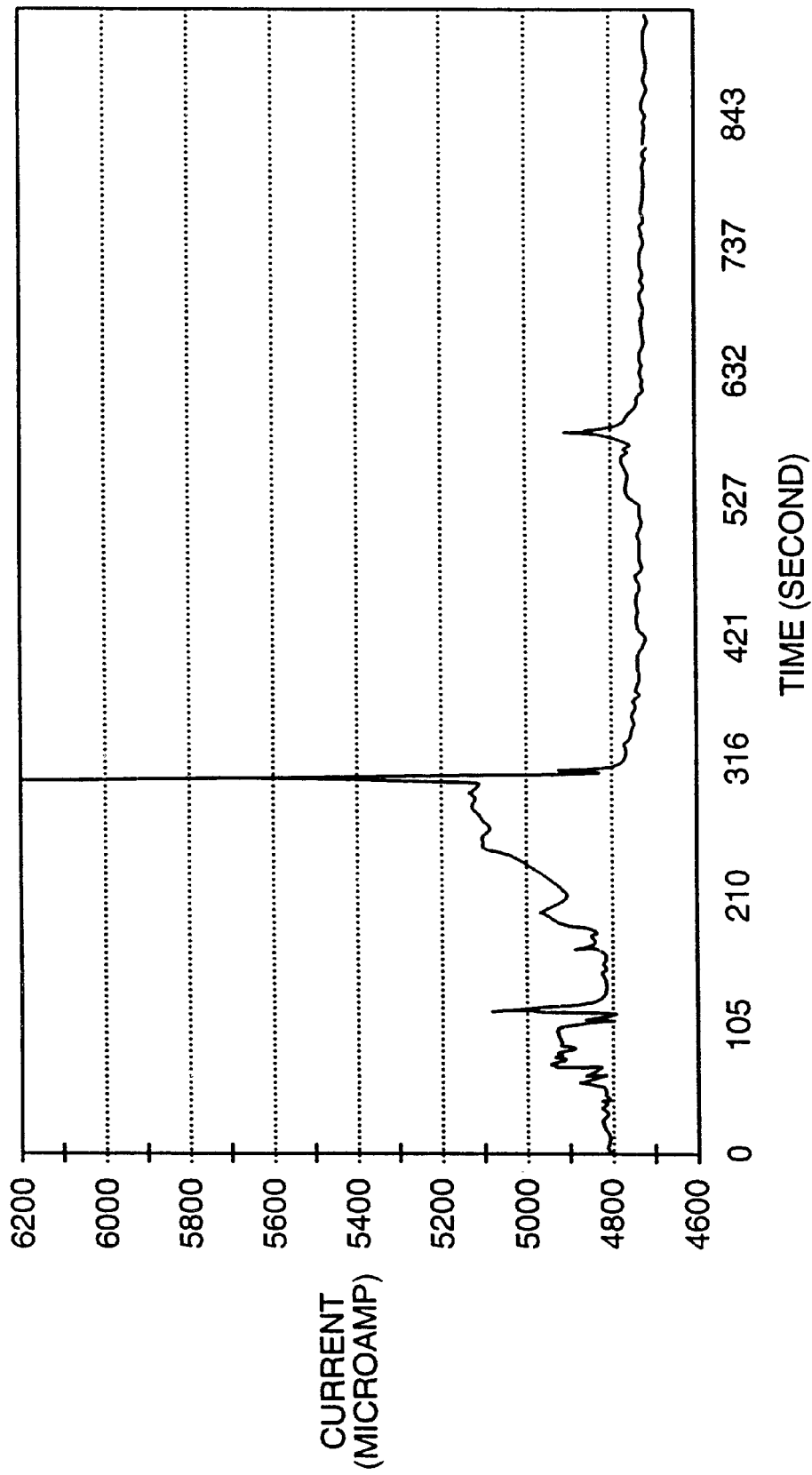
FIG. 7 shows an electropherogram of a separation performed by an embodiment of a separation apparatus.
Figure 8:
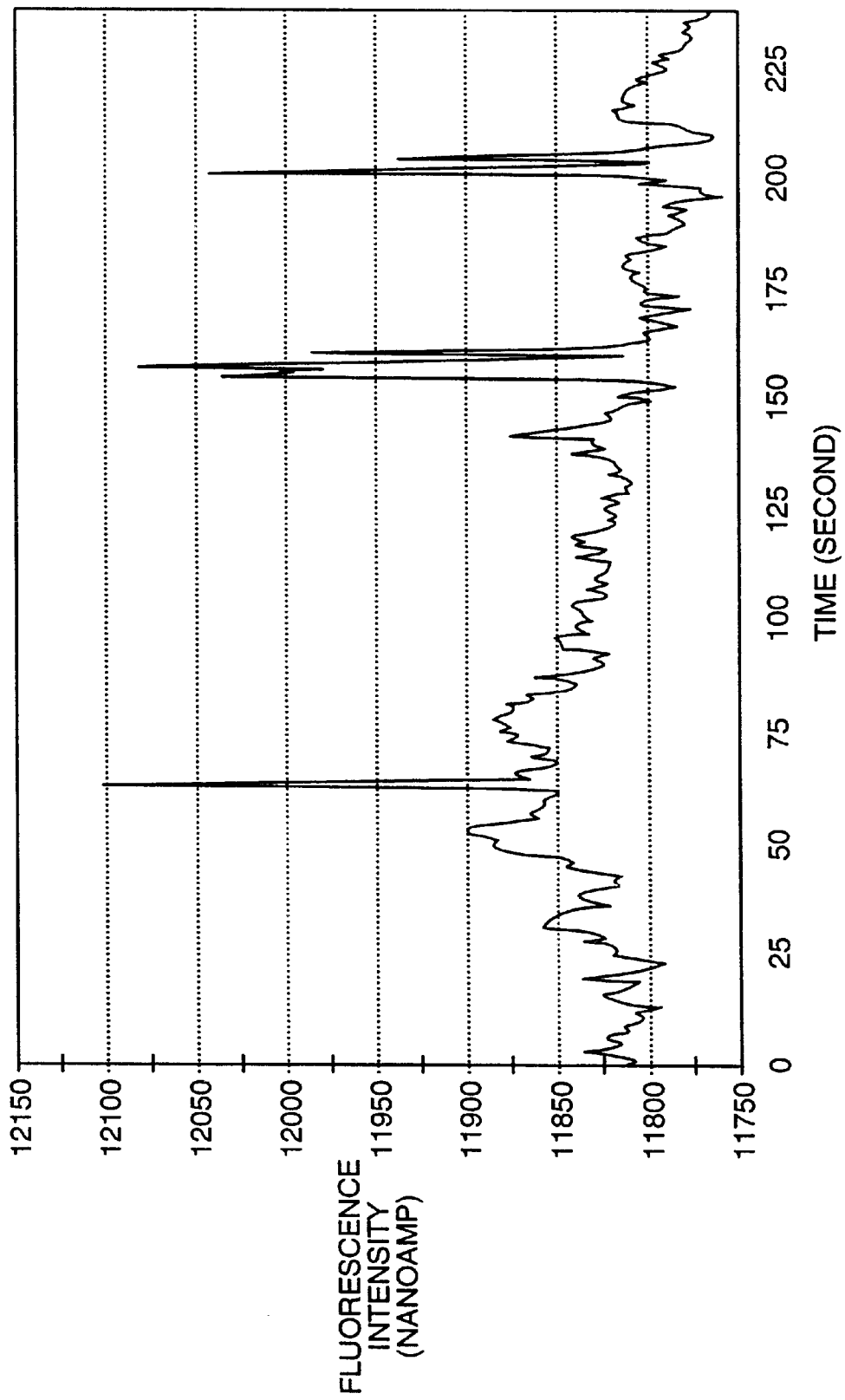
FIG. 8 shows an electropherogram of a separation performed by an embodiment of a separation apparatus.

FIG. 7 shows an electropherogram of electrophoretic separation of Rhodamine and Fluorescein using a separation apparatus of the present invention. FIG. 8 shows an electropherogram of electrophoretic separation of peptides from human growth hormone (HGH) using a separation apparatus of the present invention. The separation column of the separation apparatus used to perform the separations has a plate height of approximately one micron.

It is understood that the embodiments shown are exemplary and that it is intended to limit the scope of the invention only by the scope of the appended claims.

What is claimed is:

1. A separation device having a longitudinal axis, the separation device comprising:
   (a) a substrate;
   (b) a plurality of collocated monolith support structures, each having a first end, a second end, and a wall therebetween,
      wherein
      the first end of each collocated monolith support structure is congruent with or in contact with the substrate, and
      the plurality of collocated monolith support structures are dimensioned and oriented in a uniform two-dimensional array defining a plurality of interconnected channels bound by the walls of the collocated monolith support structures and a surface of the substrate,
         wherein the plurality of interconnected channels are non-contiguous across two adjacent collocated monolith support structures in a direction perpendicular to the longitudinal axis of the separation device; and
   (c) a channel network, the channel network comprising a plurality of monolith structures, each monolith structure having a first end, a second end, and a wall therebetween,
      wherein
      the first end of each monolith structure is congruent with or in contact with the substrate,
      the plurality of monolith structures are dimensioned and oriented to define a second set of interconnected channels which are in fluid communication with the uniform two-dimensional array of interconnected channels, and
      the number of interconnected channels in the second set of interconnected channels counted in a direction perpendicular to the longitudinal axis of the separation device comprises less than the number of interconnected channels in the uniform two-dimensional array of interconnected channels by a factor of X, where X is the number of adjacent interconnected channels of the uniform two-dimensional array of interconnected channels which combine into a single channel within the second set of interconnected channels.

2. The separation device of claim 1 wherein the second end of each collocated monolith support structure has a cross-sectional shape wherein the upstream-most point is a vertex.

3. The separation device of claim 1 wherein the second end of each collocated monolith support structure has a cross-sectional shape that is selected from the group consisting of a hexagonal cross section, a tetragonal cross-section, and a dodecagonal, cross-section.

4. The separation device of claim 3 wherein a maximum dimension of the hexagonal cross section is in the direction of the longitudinal axis of the separation device.

5. The separation device of claim 1 wherein at least the walls of the collocated monolith support structures comprise a coating.

6. The separation device of claim 5 wherein the coating comprises moieties selected from the group consisting of cationic groups, anionic groups, hydrocarbon groups, chelation groups, antibodies, antigens, and combinations thereof.

7. The separation device of claim 1 wherein the substrate comprises an electrical connector for electrical communication with an electrical source.

8. The separation device of claim 1 wherein X is two.

9. The separation device of claim 1 wherein the number of interconnected channels in the second set of interconnected channels counted in the direction perpendicular to the longitudinal axis of the separation device decreases by $X^n$, where n is the number of times the interconnected channels of the second set of interconnected channels combine along a direction of the longitudinal axis of the separation device.

10. The separation device of claim 9 wherein the number of interconnected channels in the second set of interconnected channels counted in the direction perpendicular to the longitudinal axis of the separation device becomes one.

11. The separation device of claim 1 further comprising:
   (d) a second channel network in fluid communication with the uniform two-dimensional array of interconnected channels.

12. The separation device of claim 11 wherein X is two.

13. The separation device of claim 11 further comprising a cover plate associated with the second ends of the collocated monolith support structures and the second ends of the monolith structures of the channel network.

14. A method of making the separation device of claim 13 comprising the steps of:
   etching the substrate to create the plurality of collocated monolith support structures and the plurality of monolith structures of the channel network; and
   associating the cover plate with the second ends of the collocated monolith support structures and the second ends of the monolith structures of the channel network.

15. A separation system comprising:
   the separation device of claim 13; and
   an electrophoresis apparatus in electrical communication with the separation device.

16. The separation system of claim 15 further comprising a detector in communication with the separation device.

17. The separation system of claim 16 wherein the detector comprises a mass spectrometer.

18. The separation device of claim 11 further comprising:
   (e) a third channel network in fluid communication with the uniform two-dimensional array of interconnected channels; and
   (f) a fourth channel network in fluid communication with the uniform two-dimensional array of interconnected channels,
      wherein the channel network, the second channel network, and the third channel network are adapted to define inlets to the uniform two-dimensional array of interconnected channels, and the fourth channel network is adapted to define an outlet from the two-dimensional array of interconnected channels.

19. A method of making the separation device of claim 1 comprising the step of:
   etching the substrate to create the plurality of collocated monolith support structures and the plurality of monolith structures of the channel network.

20. A separation device having a longitudinal axis of bulk liquid flow, the separation device comprising:
   (a) a substrate;
   (b) a plurality of collocated monolith support structures, each having a first end, a second end, and a wall therebetween,
      wherein
      the first end of each collocated monolith support structure is congruent with or in contact with the substrate, the plurality of collocated monolith support structures are dimensioned and oriented in a uniform two-dimensional array defining a plurality of interconnected channels bound by the walls of the collocated monolith support structures and a surface of the substrate, wherein the plurality of interconnected channels are non-contiguous across two adjacent collocated monolith support structures in a direction perpendicular to the longitudinal axis of the separation device;

(c) a channel network, the channel network comprising a plurality of monolith structures, each monolith structure having a first end, a second end, and a wall therebetween, wherein the first end of each monolith structure is congruent with or in contact with the substrate, the plurality of monolith structures are dimensioned and oriented to define a second set of interconnected channels which are in fluid communication with the uniform two-dimensional array of interconnected channels, and the number of interconnected channels in the second set of interconnected channels counted in a direction perpendicular to the longitudinal axis of the separation device comprises less than the number of interconnected channels in the uniform two-dimensional array of interconnected channels by a factor of 2;

(d) a second channel network in fluid communication with the uniform two-dimensional array of interconnected channels; and (e) a cover plate associated with the second ends of the collocated monolith support structures and the second ends of the monolith structures, wherein the cover plate comprises a surface in fluid communication with the uniform two-dimensional array of interconnected channels, the second set of interconnected channels of the channel network, and the interconnected channels of the second channel network.

21. The separation device of claim 20 wherein at least the walls of the collocated monolith support structures, the surface of the substrate, and the surface of the cover plate comprise a coating.

22. The separation device of claim 21 wherein the coating comprises moieties selected from the group consisting of cationic groups, anionic groups, hydrocarbon groups, chelation groups, antibodies, antigens, and combinations thereof.

23. The separation device of claim 20 wherein the number of interconnected channels in the second set of interconnected channels of the channel network counted in the direction perpendicular to the longitudinal axis of the separation device decreases by $2^n$, where n is the number of times the interconnected channels of the second set of interconnected channels combine along a direction of the longitudinal axis of the separation device.

24. The separation device of claim 23 wherein the number of interconnected channels in the second set of interconnected channels of the channel network counted in the direction perpendicular to the longitudinal axis of the separation device becomes one.

25. The separation device of claim 23 wherein the second channel network comprises a longitudinal axis and a third set of interconnected channels in fluid communication with the uniform two-dimensional array of interconnected channels, and the number of interconnected channels in the third set of interconnected channels of the second channel network counted in the direction perpendicular to the longitudinal axis of the second channel network of the separation device decreases by $2^n$, where n is the number of times the interconnected channels of the third set of interconnected channels of the second channel network combine along a direction of the longitudinal axis of the second channel network of the separation device.

26. The separation device of claim 25 wherein the number of interconnected channels in the third set of interconnected channels of the second channel network counted in the direction perpendicular to the longitudinal axis of the second channel network of the separation device becomes one.

27. A method of making the separation device of claim 20 comprising the steps of:

etching the substrate to create the plurality of collocated monolith support structures, the plurality of monolith support structures of the channel network and of the second channel network; and associating the cover plate with the second ends of the collocated monolith support structures and the second ends of the monolith structures of the channel network and of the second channel network.

28. A separation system comprising:

the separation device of claim 20; and an electrophoresis apparatus in electrical communication with the separation device.

29. The separation system of claim 28 further comprising a detector in communication with the separation device.

30. A monolith distributor having a longitudinal axis, the monolith distributor comprising:

a substrate; and a channel network, the channel network comprising a plurality of monolith structures, each monolith structure having a first end, a second end, and a wall therebetween, wherein the first end of each monolith structure is congruent with or in contact with the substrate, the plurality of monolith structures are dimensioned and oriented to define a set of interconnected channels, wherein the number of interconnected channels in the set of interconnected channels counted in a direction perpendicular to the longitudinal axis of the monolith distributor increases by $X^n$, where n is the number of times the interconnected channels split along the direction of the longitudinal axis of the monolith distributor and X is the number of interconnected channels into which the preceding interconnected channel splits, wherein each of the interconnected channels has a cross-sectional area measured in the direction perpendicular to the longitudinal axis of the monolith distributor, and the cross-sectional area of each of the interconnected channels decreases as the number of interconnected channels along the direction of the longitudinal axis of the monolith distributor increases.

31. The monolith distributor of claim 30 wherein X is 2.

32. The monolith distributor of claim 30 wherein the monolith distributor is adapted to be a monolith collector.

33. The monolith distributor of claim 32 wherein the number of interconnected channels in the set of interconnected channels counted in a direction perpendicular to the longitudinal axis of the monolith distributor increases from a single channel by $X^n$, and the single channel is an outlet from a chromatography column.

34. The monolith distributor of claim 30 further comprising a cover plate associated with the second ends of the monolith structures.

35. The monolith distributor of claim 30 wherein the monolith distributor is adapted for use in a chromatographic application, an electrophoretic application, or an electroosmotic application.

36. The monolith distributor of claim 30 wherein the number of interconnected channels in the set of interconnected channels counted in a direction perpendicular to the longitudinal axis of the monolith distributor increases from a single channel by $X^n$, and the single channel is an inlet to a chromatography column.

* * * * *